United States Patent [19]
Patt

[11] 4,291,229
[45] Sep. 22, 1981

[54] SUPPORT AND RESTRAINING DEVICE FOR ARTHOGRAPHIC EXAMINATION OF THE KNEES

[76] Inventor: Kenneth W. Patt, 5131 Warren Rd., Imperial, Mo. 63052

[21] Appl. No.: 101,675

[22] Filed: Dec. 10, 1979

[51] Int. Cl.³ .................. G21K 5/08; G03B 41/16; H01J 37/20
[52] U.S. Cl. ................. 250/451; 250/456; 250/476; 250/491; 269/328
[58] Field of Search ............. 250/456, 451, 491, 521, 250/476, 439 R, 444, 446; 269/328; 128/134

[56] References Cited

U.S. PATENT DOCUMENTS

| | | | |
|---|---|---|---|
| 3,025,397 | 3/1962 | Travis et al. | 250/451 |
| 3,302,021 | 1/1967 | Hardy | 250/451 |
| 3,766,384 | 10/1973 | Anderson | 250/446 |
| 3,790,803 | 2/1974 | Phillips | 250/491 |
| 3,979,595 | 9/1976 | Merchant | 250/451 |
| 4,045,678 | 8/1977 | Rickard | 250/451 |
| 4,181,297 | 1/1980 | Nichols | 269/328 |

FOREIGN PATENT DOCUMENTS 726482  5/1932  France ................ 250/456

OTHER PUBLICATIONS

Westall, "Arthrography: A Critical Study of the Technique and Possible Improvement of Knee Arthrograms", Radiologic Technology, vol. 45 (5), 1974, pp. 311-321.

Freiberger et al., "Arthrography of the Knee by Double Contrast Method", Amer. J. Roentgenol, vol. 97, Jul. 1966, pp. 736-747.

Andren et al., "Double-Contrast Arthrography of Knee with Horizontal Roentgen Ray Beam", Acta. Orthro. Scandinav. 29, 1960, pp. 307-314.

*Primary Examiner*—Alfred E. Smith
*Assistant Examiner*—Carolyn E. Fields
*Attorney, Agent, or Firm*—Richard J. Sher

[57] ABSTRACT

Arthrograms of the knee permit visualization of the soft tissue components of the knee joint. This is particularly important in the diagnosis of lesions of the menisci, especially tearing lesions. A device is disclosed which includes a novel clamp for supporting and restraining the patient's leg in a precise position in front of a unique film holder. A novel arthrographic protractor indicator is also provided to permit the technician to accurately identify the exact degree of knee rotation depicted in each radiograph. The device is uncomplicated, compact, and is constructed in a uniquely adjustable manner which permits accurate arthrographic studies of either the right or left knee in any size of individual. The arthrogram radiographs obtained with this device are clearer, more accurate and precisely reproducible, if necessary. All of these advantages are accompanied by greater comfort and far less radiation exposure to the patient, and to the radiological personnel.

8 Claims, 5 Drawing Figures

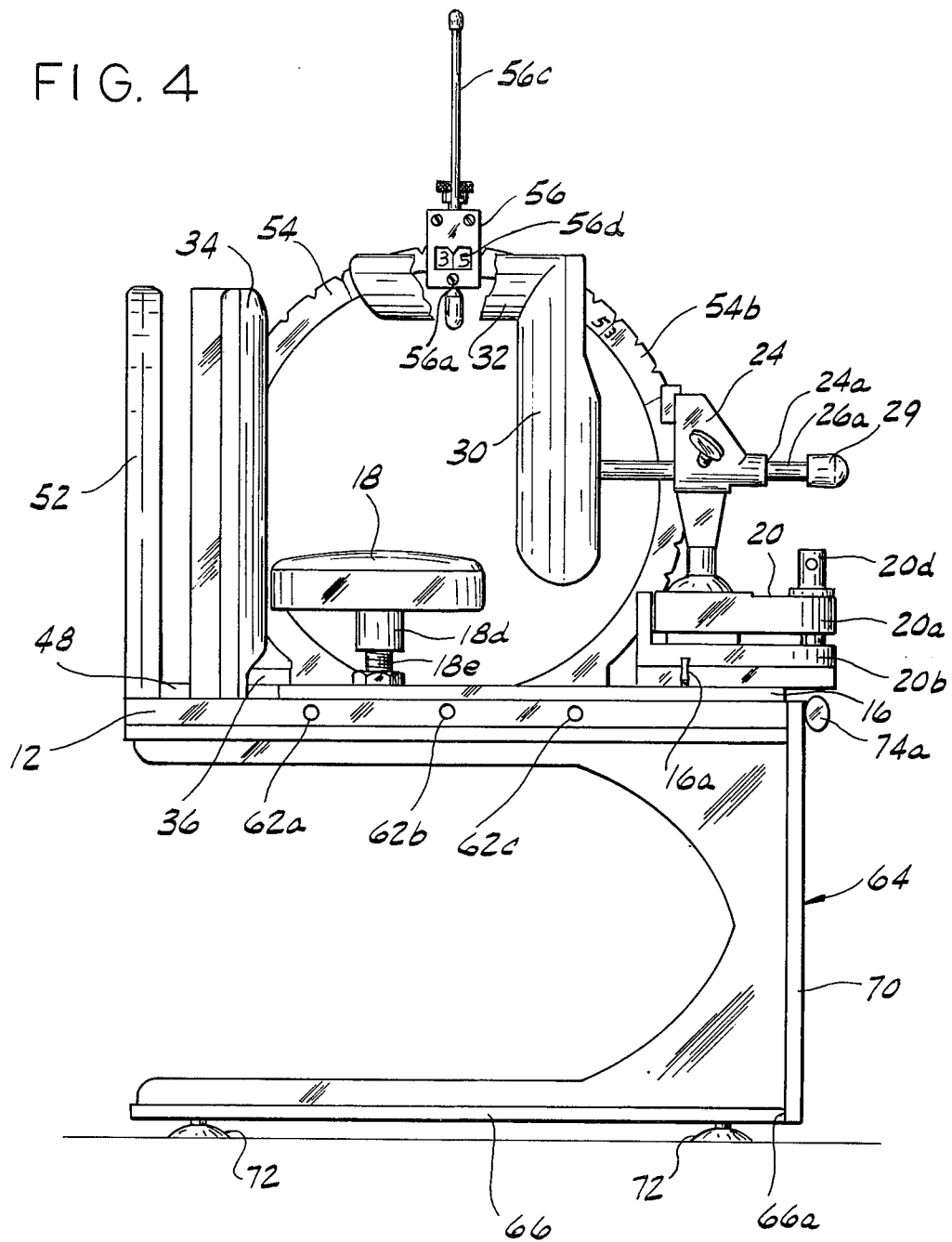

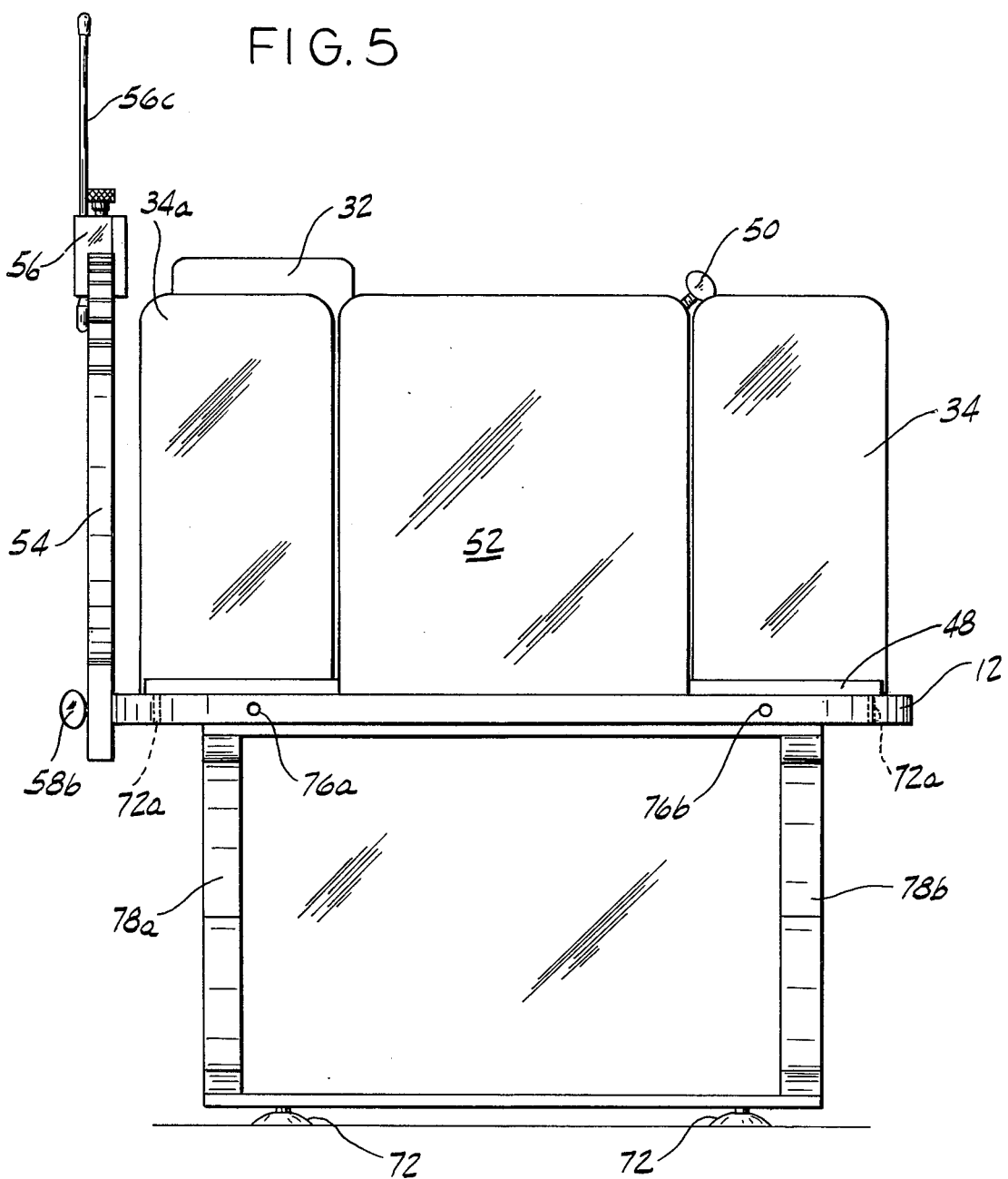

SUPPORT AND RESTRAINING DEVICE FOR ARTHOGRAPHIC EXAMINATION OF THE KNEES

BACKGROUND AND SUMMARY OF THE INVENTION

The invention relates to a new support and restraining device for arthrographic examination of the knees.

Arthrographic examination of the knees is a well known radiologic procedure for diagnosing lesions of the menisci which lie between the articulating surfaces of the knee joint. A complete description of the history of the technique, the anatomy of the knee joints and common arthrographic procedures and collateral leg supporting devices appear in a paper by Donald R. Westall entitled "Arthrography: A Critical Study of the Technique and Possible Improvement of Knee Arthrograms," Radiologic Technology, Vol. 45, No. 5, p. 311-321, 1974. Other monographs describing arthrography of the knee are by Freiberger et al, "Arthrography of the Knee by Double Contrast Method," Amer. J. Roentgenol, Vol. 97: 736-747, July, 1966; and by Andren et al, "Double-Contrast Arthrography of Knee with Horizontal Roentgen Ray Beam," Acta Orthro. Scandinav. 29: 307-314, 1960. All the material contained in the above articles is incorporated herein by reference thereto.

For convenience, a short description of the known arthrographic procedures are described hereinbelow.

All arthrographic procedures involve the injection of a contrast medium into the joint space surrounding the knee joint. The contrast medium envelopes and coats the menisci of the knee joint, thereby allowing the outline thereof to be visible on radiographs. By this means pathology of the menisci, and especially tears, can be detected.

There are three basic techniques for producing the radiographs for an arthrographic examination. These are: (1) the vertical ray technique (2) the fluoroscopic technique, and (3) the horizontal ray technique. The vertical ray technique utilizes a downwardly projecting X-ray beam through the knee joint. For reasons unimportant to this disclosure, this technique has not been widely utilized since the development of the fluoroscopic technique. The Fluoroscopic technique allows the radiologist to view the knee joint continually as it is rotated, thereby allowing him to evaluate both menisci in different projections. The main disadvantage of fluoroscopy is that the patient, radiologist, and the technologist are exposed to a great deal of unnecessary radiation. The best method for making an arthrographic study of the knee is by utilization of the horizontal ray technique. As the name implies, a standard X-ray machine is used to produce a horizontal X-ray beam which is made to pass through the patient's knee and onto a standard radiographic film cassette. Up to the present time, as shown in the article by Andren et al, supra, this has been performed by placing a small pillow under the patient's knee joint and a sandbag upon the ankle. This procedure flexes the knee joint and allows clear radiographs of the knee menisci to be obtained. While this is a reasonably good method of obtaining an arthrographic study of the knee joint, it is difficult, if not impossible, to accurately localize a lesion which has been discovered on a radiograph. This is due to the inability of the radiologist to determine the exact position of the knee during each radiographic exposure. Further, since the leg is not restrained, and the rotation of the knee about the femoral axis is not recorded, a particular projection cannot be accurately duplicated for more precise study. Also, the so-called sand bag technique shown by Andren et al, supra, does not insure that the patient's leg is held in the correct orientation with respect to the film holder and therefore the accuracy of the radiograph must always be, to some degree, suspect. Further, since the leg is not fully restrained from movement, the possibility of a blurred radiograph is always present.

The present invention relates to a support and restraining device which greatly improves the accuracy and reproducibility of radiographs produced using the horizontal Roentgen ray technique of knee arthrography. The device includes: a main horizontal base or platform which supports a novel leg clamping unit, a unique film holder, and a device for precisely indicating the degree of rotation of the patient's leg, the latter of which will be referred to herein as an arthrographic protractor.

The clamp unit includes a vertically adjustable horizontal support member which is adapted to support the weight of the patient's leg above the platform and an adjustable restraining device which quickly and easily secures the leg in a selective position on the support member. The restraining device secures the lower femoral section of the leg above the platform to permit the free end of the leg to cantilever downwardly under the force of gravity to thereby stress the knee in order to open the knee joint. This stressing or opening of the knee joint is necessary to produce clear, diagnostic radiographs. The clamp unit is situated on the platform with respect to the film holder so that the femur can always be restrained in a line parallel to the plane of the film holder. This construction again helps to provide accurate, reproducible radiographs of the knee.

The film holder includes a film elevator which adjusts the vertical level of the film in a facile manner in order to place an unexposed film frame directly behind the area of the knee to be examined. The film holder is also provided with an X-ray beam restricting frame for automatically producing a series of the most advantageously sized radiographs of the knee on a single film cassette. Also, the film holder is provided with film markers which, with a touch of the finger, will indicate on the radiograph whether the image is of the left or right leg and whether the meniscus being radiographed is the medial or lateral.

The support and restraining device is uniquely designed so that the clamp unit and the arthrographic protractor can be adjustably located on the platform to permit the examination of either leg of the patient without unnecessary discomfort to the patient.

The underside of the platform is provided with suction cups so that the device may be placed directly upon an X-ray table in a stable manner. Also, in keeping with the versatility of the device, a support for the main base, or understructure, is provided, also with suction cups therebelow. The understructure includes top and bottom horizontal members which are held apart by an upstanding wall member secured to parallel edges of the top and bottom horizontal members, which edges lie in the same vertical plane, and the distance between the top and bottom members is sufficient to permit the other leg of an adult patient to be rested therebetween. This feature not only aids in precisely positioning the knee to be studied with maximum patient comfort, but also allows the patient to continually roll his body as the leg supported in the device is incrementally turned when a series of radiographs are taken about one side of the knee, for example, the medial side of the right leg. A target film distance (TFD) indicator is also incorporated on the platform in order to aid the technician in quickly measuring the distance between the X-ray tube and the film.

It is therefore one of the main objects of the invention to provide a clamp unit which can be used quickly to position and secure a patient's knee in front of a film holder and which can easily release the leg for repositioning and subsequent resecurement.

It is another main object of the invention to provide a clamp unit which is vertically adjustable above a platform and which will support and restrain the lower femoral section of a patient's leg, be it an adult or a child, and which will thereby permit stress to be applied to the knee in order to open the joint for arthrographic study.

A further main object of the invention is to provide a radiographic film holder which is vertically adjustable, is provided with means to mark which leg and which side thereof is shown in the radiograph, and which automatically restricts the size of a single radiograph exposed on the radiographic film.

It is another main object of the invention to provide a support and restraining device for arthrographic examination of either the right or the left knee and either the lateral or medial side thereof with maximum patient comfort, while minimizing the amount of unnecessary radiation to which the patient is exposed.

It is still another main object of the invention to provide an uncomplicated, compact, and adjustable assembly which allows arthrogram radiographs to be obtained which are clearer, more accurate, and if necessary, precisely reproducible.

These, as well as other objects and advantages of the invention will become more apparent upon a reading of the following detailed description of a preferred embodiment, in conjunction with the drawings, wherein:

BRIEF DESCRIPTION OF THE DRAWINGS

FIG. 4 is a side elevational view of the device showing the side opposite to that shown in FIG. 2; and FIG. 5 is a rear elevational view of the device.

DETAILED DESCRIPTION OF A PREFERRED EMBODIMENT

With reference to the drawings, there is shown a preferred form of a support and restraining device, generally referred to by the numeral 10, for arthrographic examination of the knee joint, and which is constructed and which will operate in accordance with the principles and objects of the present invention. Support and restraining device 10 includes a planar main base or platform 12 which is generally rectangular with rounded corners and constructed of any rigid material, but preferably of heavy gauge aluminum. Platform 12 supports thereon a clamp unit 14 adjacent one side thereof.

Figure 1:
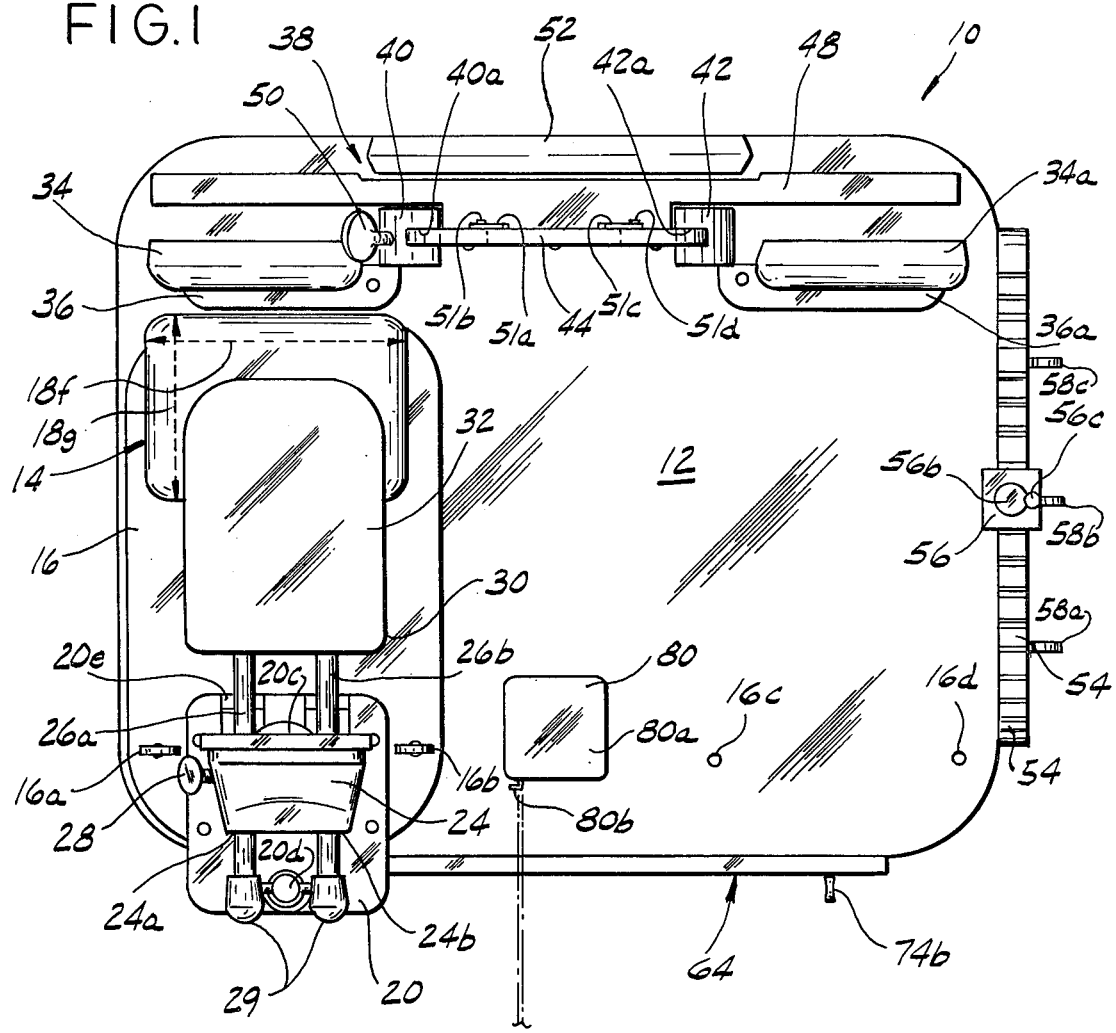
FIG. 1 is a top plan view of a preferred embodiment of a support and restraining device for arthrographic examination of a knee according to the principles of the invention.
Figure 2:
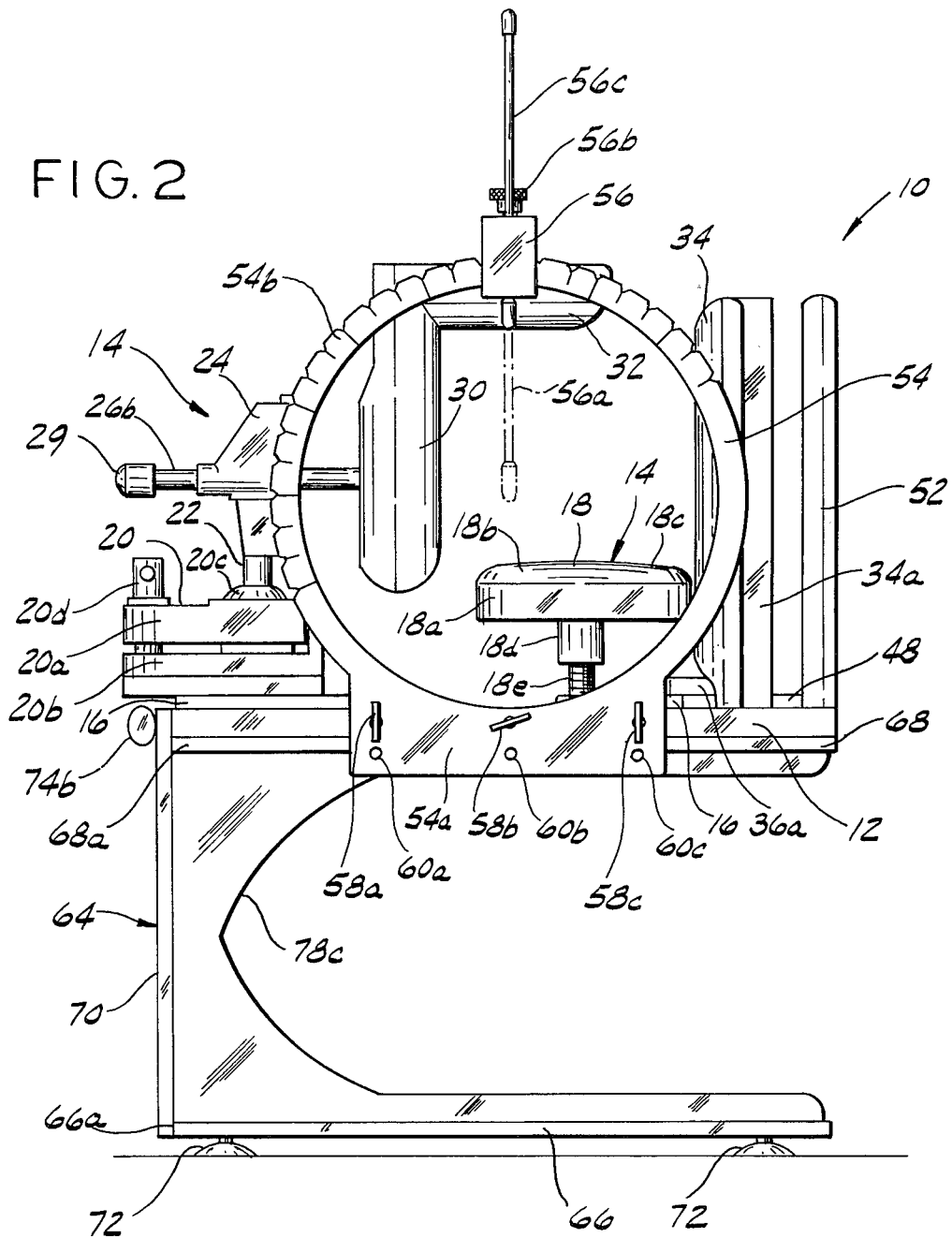
FIG. 2 is a side elevational view of the device.

As best seen in FIGS. 1, 2, and 4, clamp unit 14 includes a planar traction base member 16, constructed of a generally rectangular piece of rigid material such as aluminum and has rounded corners. Affixed to and supported upon base member 16 is a lower vertical traction device or pad 18 and a universal locking device 20. Lower vertical traction device 18 includes a planar rigid member 18a having a suitable padding media such as foam rubber 18b thereon, and which is held thereon by an appropriate covering 18c such as leather or vinyl. On the underside of lower vertical traction device 18 there is affixed internally threaded bushing 18d which is threadingly engaged with upwardly directed externally threaded rod 18e. The threaded interengagement of bushing 18d and rod 18e provides a simple and inexpensive means for vertically adjusting the height of traction device 18. Further, pad 18 is rectangular, having a relatively long dimension 18f and a relatively short dimension 18g (See FIG. 1). The rectangular configuration of pad 18 provides a conveniently sized support for a child's leg in the position shown, and a properly sized support for an adult leg when the pad is turned ninety degrees upon rod 18e.

Universal locking device 20 is comprised of upper and lower members 20a and 20b, respectively, which are hinged at 20e. Adjustable ball 20c is located within a socket formed by upper and lower members 20a and 20b, respectively. Screw member 20d, when rotated, acts to adjust the distance between upper and lower members 20a and 20b and thereby when tightened freezes ball 20c in any desired position and when loosened allows ball member 20c to be pivoted about the center thereof. Extending upwardly from universal locking device 20 and more specifically from ball member 20c is a support rod 22 which carries support block 24. A pair of rearwardly directed, parallel bores 24a and 24b extend horizontally through block 24 and carry therein a pair of support rods 26a and 26b, respectively. Each of rods 26a and 26b are slideable within bores 24a and 24b, respectively, and may be locked in a selected position with respect to block 24 by means of locking screw 28 extending through block 24 into bore 24a. On the forward end of each of rods 26a and 26b there is affixed a stop member 29 which prevents the forward portions of rods 26a and 26b from sliding free of bores 24a and 24b, respectively. On the rearward ends of rods 26a and 26b there is located a planar lateral traction device 30. Secured to the top edge of lateral traction device 30 is an upper vertical traction device member 32. Upper vertical traction device 32 is generally planar and extends at a ninety degree angle from the plane of lateral traction device 30. Both traction devices 30 and 32 are constructed similarly to lower vertical traction device 18 in that they are constructed of a padded rigid material having a covering therearound. Clamp unit 14 also includes a stationary traction device 34 which is mounted on an elongated member 36 affixed in a stationary manner on platform 12. Stationary traction device 34 is also constructed of a rigid material which has been padded and subsequently provided with a suitable covering. Vertically adjustable support member 18 in conjunction with stationary lateral traction member 34 and universally adjustable traction members 30 and 32 act to support and restrain the lower femoral section of a patient's leg for proper positioning thereof during an arthrographic study of a knee, as will be explained in greater detail hereinbelow.

A second stationary traction device 34a is supported upon a second elongated member 36a which is affixed to platform 12. Traction devices 34 and 34a lie in the same vertical plane but are positioned adjacent opposite sides of platform 12, as shown in FIG. 1. As best seen in FIG. 1, traction base 16 may be removed from platform 12 by hand removal of locking screws 16a and 16b and thereafter traction base 16 along with support pad 18 and traction members 30 and 32 may be repositioned on the other side of platform 12 adjacent stationary traction member 34a and secured thereat by locking engagement between locking screws 16a, 16b and internally threaded bores 16c, 16d. Relocation of traction base 16 in the manner described above provides for greater versatility of device 10 as will be explained further hereinbelow.

Figure 3:
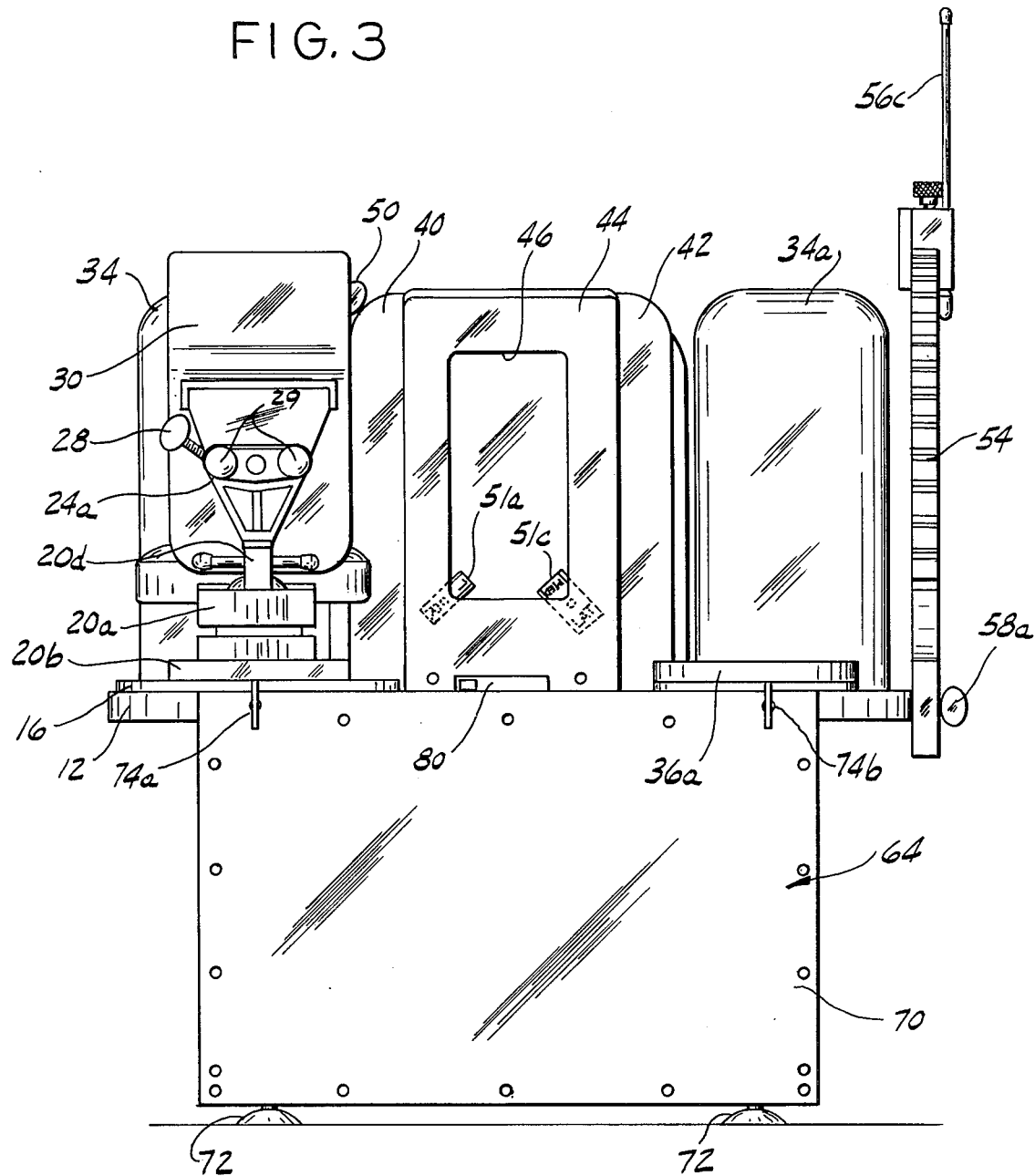
FIG. 3 is a front elevational view of the device.

Mounted slightly rearward and generally between stationary traction devices 34 and 34a is a radiographic film holder 38 including a pair of upstanding pillars 40 and 42 securely affixed to platform 12. Each of pillars 40 and 42 include a vertically extending groove 40a and 42a, respectively, facing one another. Slideably engaged within grooves 40a and 42a is a metal frame 44 which forms a rectangular opening 46 therethrough. Attached to the rearward side of frame 44 at the lower extremity thereof is an elongated film elevator 48 which is adapted to carry a film cassette (not shown) and which by virtue of its secure attachment to frame 44 will act to raise, and lower the film cassette, along with frame 44. While frame 44 is sized to be vertically positioned in grooves 40a and 42a by frictional engagement therein, frame locking screw 50 passes through pillar 40 into groove 40a, and selectively locks frame 44 in a desired vertical orientation. Attached at one lower corner of frame 44 is a right/left film marker 51a comprised of a ribbon of metal marked on one end with an R and on the other end with an L, and pivotable on a central pin 51b such that either the "R" or the "L" may be interposed in front of the film in order that the letter may appear on the developed film. At the other lower corner of frame 44 is a lateral/medial film marker 51c having a like configuration as that of marker 51a and being pivotable on pin 51d, except that marker 51c is marked with "MED" on one end thereof and "LAT" on the other end thereof (See FIG. 3).

Directly behind frame 44 and film elevator 48 there is located on platform 12 a vertically extending backplate 52 which is comprised of a three-quarter inch aluminum plate contiguously mounted with a one-quarter inch lead plate and having a covering therearound. Backplate 52 will block and absorb the majority of the X-rays passing through a film cassette (not shown).

As shown in the drawings, a leg rotation indicator assembly or arthrographic protractor 54 is mounted on platform 12 on the side of the platform opposite traction base 16, such that when the lower femoral section of a patient's leg is restrained in clamp unit 14, the calf portion of the leg will extend through protractor 54. Protractor 54 is preferably fabricated of aluminum, and, as best seen in FIG. 2, includes a lower base section 54a and circular frame section 54b integral with base 54a. Riding along the major portion of the periphery of circular frame 54b is an indicator 56 which includes radially inwardly projecting pointer 56a and spring-loaded locking knob 56b. A pointer casing 56c extends upward, radially outward from indicator 56 and telescopically engages pointer 56a, thereby permitting pointer 56a to radially extend toward or withdraw from the central axis of frame 54, as indicated by the phantom lines in FIG. 2. Frame 54b is notched around approximately one-hundred-eighty degrees of the outer circumferential surface, each notch representing seven and one half degrees of circular frame 54b. In order to move indicator 56 on frame 54b, knob 56b is pulled outwardly against a spring force, thereby withdrawing a pin (not shown) from a particular notch. When indicator 56 is positioned on frame 54b at a desired location, knob 56b is released and the pin attached thereto engages a notch thereby captively retaining indicator 56 in the desired location. Numerical indicia printed upon the frame 54b (only partially shown) indicate to the operator the rotational position of indicator 56, and said indicia may be seen through a window 56d in indicator 56.

As seen in FIG. 2, base section 54a of arthrographic protractor 54 is attached to the edge of platform 12 which is opposite to the side on which traction base 16 is located, by means of three locking screws 58a, 58b, and 58c. Three holes 60a, 60b, 60c, located in base section 54a permit protractor 54 to be elevated when necessary simply by repositioning locking screws 58a, 58b, 58c into the existing internally threaded holes in the edge of platform 12. Further, when traction base 16 is repositioned on the opposite side of platform 12 from that shown in the drawings, and as described hereinabove, then protractor 54 is removed from platform 12 and repositioned on the opposite side thereof by means of internally threaded holes 62a, 62b, 62c in the opposite edge of platform 12 (See FIG. 4).

Platform 12 is positionable upon an understructure 64 fabricated of aluminum plate material or the like and includes a bottom horizontal member 66, a top horizontal member 68 and an upstanding wall member 70 which is secured to respective vertically aligned edges 68a, 66a, of top and bottom horizontal members 68 and 66, respectively. The height of wall member 70 is such that the distance between horizontal members 66 and 68 will be sufficient to permit an adult patient's leg to be rested therebetween. The underside of bottom horizontal member 66 is provided with four internally threaded bores into which may be secured four downwardly facing suction cups 72 for secure placement of the understructure on an examining table or the like (not shown). Platform 12 rests on the upper surface of upper horizontal member 68 and is secured from movement relative thereto by platform locking screws 74a, 74b, which pass through the upper extremity of wall member 70 and into internally threaded bores (not shown) in the front edge of platform 12. Internally threaded bores 76a, 76b located in the rear edge of platform 12 permit platform 12 to be shifted one-hundred-eighty degrees on understructure 64 simply by removing locking screws 74a, 74b and repositioning them within bores 76a, 76b. Understructure 64 also includes reinforcement braces 78a, 78b for aiding in the support of platform 12. Support braces 78a, 78b have a rounded inner surface 78c, and do not interfere with the positioning of a patient's leg beneath platform 12 and between horizontal members 66 and 68. It is noted that platform 12 may be removed entirely from understructure 64 by removing locking screws 74a and 74b, and four internally threaded bores 72a (shown in phantom line) in the underside of platform 12 permit the attachment of four suction cups beneath platform 12 to thereby allow platform 12 to be securely positioned on a table or the like. Understructure 64 is not used when examining a patient in the prone position or when examining a child.

Affixed to platform 12 directly in front of film holder 38 is located a linear measuring or target film distance (TFD) indicator 80 comprising a housing 80a holding a retractible measuring tape 80b. Housing 80a is affixed to platform 12 at a preselected distance from film holder 38 and tape 80b indicates the precise location at which the X-ray tube should be located with respect to film holder 38.

OPERATION

The preferred embodiment of the arthrographic support and restraining device 10 may be utilized to examine the soft tissue of the knee as follows:

Device 10 as shown in the drawings is set up as it would be for an examination of the left-medial or right-lateral aspect of the knee. Assuming an examination of the right-lateral knee is to be performed, the knee is injected with positive and negative contrast media according to the double contrast technique explained in the monographs cited hereinabove. The positive contrast medium used is usually a water-soluble, iodine containing substance and the negative contrast medium is air. Device 10 is positioned on an examining table; suction cups 72 providing secure placement thereof. Measuring tape 80b of target film distance indicator 80 may conveniently be used to position the X-ray tube (not shown) at the proper distance forward of film holder 38.

Lower vertical traction device 18 is turned upon threaded rod 18e until traction device 18 is at the proper height for the particular patient and for the particular positioning of the knee desired for a specific arthrogram so that the correct amount of stress or opening of the knee joint is obtained by the gravitational pull of the patient's lower leg. When the proper height has been located, device 18 is turned within a ninety degree setting to provide either a relatively wide support 18f for thicker legs, or a relatively narrow support 18g, for thinner legs. As shown in FIG. 1, device 18 is set to support a relatively thin leg.

The patient is positioned on his back and the right, lower femoral section, i.e., the leg just above the knee, is placed on device 18, and the leg is pressed up against stationary traction device 34 such that the femur is located in a plane parallel to that of device 34 and, accordingly, parallel to the plane of film holder 38 and the film (not shown). When the knee joint of the patient is located directly in front of frame 44, locking screw 50 is loosened to permit the vertical adjustment of frame 44 and film elevator 48 so that the knee joint is in vertical alignment with rectangular opening 46 in frame 44; thereafter locking screw 50 may be tightened. Film markers 51a and 51c are pivoted such that the "R" of marker 51a and the "LAT" of marker 51c are interposed into opening 46, thus conveniently providing the designation of Right/Lateral on the finished radiograph.

Simultaneously, screw member 20d and locking screw 28 are loosened allowing the junction line of lateral traction device 30 and vertical traction device 32 to tilt toward the axis of the femur and permit devices 30 and 32 to firmly, yet comfortably, engage the leg of the patient and thereby restrain the leg in proper position against pad 18 and lateral traction member 34. Thereafter, both locking screw 28 and screw member 20d are tightened to maintain secure engagement and retention of the leg.

At this point the patient's lower leg is of course positioned through circular frame 54b of arthrographic protractor 54. Indicator 56 is positioned on frame 54b in a reference position and pointer 56a is withdrawn from casing 56c until pointer 56a touches the leg. A mark is made on the leg at the location of engagement between pointer 56a and the leg.

A film cassette (not shown) containing a large sheet of film is placed upon film elevator 48 such that only one small rectangular portion of the film will be exposed to the X-ray beam through frame 44 during each radiograph exposure. (It is noted that interchangeable frames 44 having larger or smaller openings 46 may be provided according to the size of the exposure desired). After the first and each successive radiograph is taken, the film cassette is repositioned to place an unexposed portion thereof directly behind opening 46 of frame 44.

Also, after the first and each successive radiograph is taken, indicator 56 is moved to a different notch on circular frame 54b, and the patient's leg is turned slightly in clamp unit 14 so that the mark previously made on the leg again corresponds to the position on pointer 56a. The technician makes a note of the location of indicator 56 on the arthrographic protractor 54, and thereby can tell the radiologist the precise angle and position of the knee depicted in each radiograph.

The provision of arthrographic protractor 54 permits the technician to take a series of radiographs of the knee as the knee is turned to a precise angle between successive radiographs. Thereafter, if the radiologist feels he has located a tear or other pathology in a particular exposure, but cannot be sure, the radiologist can direct the technician to duplicate the radiograph by repositioning the leg precisely as it was in the suspect radiograph and can further instruct the technician to take additional radiographs of the leg as it is turned in only 7.5° increments (which in the preferred embodiment equals a single notch on the protractor frame 54b). This exacting procedure will provide the radiologist with the additional and precise information he needs to make an objective determination of the condition of the soft tissue, especially the menisci of the knee.

As the patient's leg is successively turned counterclockwise, he may comfortably pivot his body so that the left leg will rest between top and bottom horizontal members 68 and 66, respectively, of understructure 64.

In order to make an arthrographic study of the right medial aspect of a patient's knee, for example, device 10 is simply and quickly modified by hand in the following manner. Locking screws 16a and 16b are removed from threaded bores (not shown) in platform 12. Traction base 16 is then lifted from its position on platform 12 and relocated in front of stationary traction device 34a. Thereafter, locking screws 16a and 16b are hand tightened into bores 16c and 16d in platform 12. It is noted that the rearward edge of traction base 16 is positioned beneath a forwardly projecting lip on members 36 and 36a in order to provide greater stability to the assembly. Arthrographic protracter 54 is also relocated to the opposite side of platform 12 by removing locking screws 58a, 58b, 58c and resecuring same into bores 62a, 62b and 62c in the other edge of platform 12. As hereinabove noted, protractor 54 may be secured in an upper or lower position according to the set of bores on base section 54a utilized. Film marker 51a is turned to show in opening 46 the "R" thereon, to indicate that the radiographs are of the right knee and marker 51c is pivoted to show "MED" to indicate the medial or inner area of the knee. At this time device 10 is ready to help obtain a series of radiographs of the right medial knee pursuant to the procedure set forth above with respect to the left knee.

When studying the leg of a small person such as a child, or the leg of a patient who is to be studied in the prone position, the understructure may be removed by removing locking screws 74a and 74b. Thereafter, the platform 12 may be placed directly on the X-ray table to significantly reduce the height of pad 18. Suction cups 72 may be removed from understructure 64 and attached to the underside of platform 12 to provide greater stability.

Also, if desired for greater patient comfort, understructure 64 may be placed under platform 12 in a position one-hundred-eighty degrees from that shown in the drawings by inserting locking screws 74a and 74b in threaded bores 76a and 76b in the rearward edge of platform 12.

It can be readily seen from the foregoing that a support and restraining device has been disclosed which will provide the objects and advantages specifically enumerated above, as well as other incident objects and advantages.

It is of course evident that numerous changes can be made to the preferred embodiment described hereinabove without departing from the spirit and scope of the present invention. It is therefore noted that the scope of the invention should not be restricted by details enumerated above with respect to the foregoing description of the preferred embodiment, but that the scope of the invention should be defined by the language of the following claims.

What is claimed is:

1. A support and restraining device for arthrographic examination of a knee, comprising:
    a horizontal platform;
    a clamp unit means mounted on said platform for supporting and restraining a patient's leg above said platform;
    said clamp unit means including a vertically adjustable horizontal support member adapted to support the weight of such leg above said platform and an adjustable restraining means for securing such leg in a selective position on said support member and for permitting stress to be applied to such knee in order to open the knee joint; an upstanding member adjacent one side of said support member and a pressure member mounted adjacent the side of said support member opposite said one side;
    said pressure member being supported on said platform by adjustable positioning means which provide selectively adjustable and secure placement of said pressure member with respect to said support member and said upstanding member
    said pressure member having a first generally planar section positioned so as to generally face said upstanding member and a second generally planar section immovably secured to said first section and positioned over and in generally facing relationship with said support member;
    said adjustable positioning means including a universal joint unit for selective tilting and secure location of said pressure member with respect to said platform and a linear adjustment means for selective movement of said pressure member towards and away from said upstanding member and said support member and for secure location with respect thereto.

2. The device as specified in claim 1 and further characterized by:
    said platform being selectively supportable by an understructure;
    said understructure including a bottom horizontal member and a top horizontal member;
    said top and bottom horizontal members being held apart by an upstanding wall member secured to respective edges of said top and bottom horizontal members lying in the same vertical plane wherein the distance between said top and bottom members is sufficient to permit a patient's leg to be rested therebetween.

3. The device as specified in claim 2 and further characterized by:
    said bottom horizontal member having a planar underside adapted to hold downwardly facing suction cups for secure placement on a flat surface.

4. The device as specified in claim 2 and further characterized by:
    said platform being manually removeable from said understructure.
    linear measuring means secured on said platform for measuring the distance between a film cassette and an X-ray beam producing machine.

5. The device as specified in claim 1 and further characterized by:
    a radiographic film holder vertically mounted on said platform; said film holder lying in a plane generally parallel to said upstanding member;
    a second upstanding member on said platform spaced from and located coplanar with said first-mentioned upstanding member;
    said pressure member and said support member being moveable between a first location on said platrorm wherein said pressure member and said support member clampingly cooperate with said first-mentioned upstanding member, and a second location on said platform wherein said pressure member and said support member clampingly cooperate with said second upstanding member.

6. The device as specified in claim 1 and further characterized by:
    a radiographic film holder vertically mounted on said platform;
    said film holder having a first vertical edge and a second vertical edge;
    film support means between said first and second edges;
    said clamp unit means bein selectively positionable on said platform between a first position adjacent said first edge of said film holder and a second position adjacent said second edge of said film holder.

7. The device as specified in claim 6 and further characterized by:
    said platform being selectively supportable by an understructure;
    said understructure including a bottom horizontal member and a top horizontal member;
    said top and bottom horizontal members being held apart by an upstanding wall member secured to respective edges of said top and bottom horizontal members lying in the same vertical plane wherein the distance between said top and bottom members is sufficient to permit a patient's leg to be rested therebetween.

8. The device as specified in claim 7 and further characterized by:
said platform being selectively positionable on said understructure whereby said upstanding wall member may be positioned adjacent one side of said platform which is adjacent to said film holder or said upstanding wall member may be positioned adjacent the side of said platform opposite said one side of said platform.

* * * * *